(12) United States Patent
Yavitz

(10) Patent No.: US 6,364,098 B2
(45) Date of Patent: *Apr. 2, 2002

(54) SOFT CONTACT LENS CLEANING AND STORAGE SYSTEM

(75) Inventor: Edward Q. Yavitz, Rockford, IL (US)

(73) Assignee: Third Millenium Trust, Scotsdale, AZ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/289,472

(22) Filed: Apr. 9, 1999

(51) Int. Cl.[7] .............................................. A45C 11/04
(52) U.S. Cl. ..................... 206/5.1; 15/104.92; 53/428; 206/38
(58) Field of Search ................ 206/5.1, 223, 38; 15/214, 104.92, 104.93, 244.1; 134/901, 15, 28; 422/292, 300; 53/428, 467; 604/11

(56) References Cited

U.S. PATENT DOCUMENTS

| | | | |
|---|---|---|---|
| 3,089,500 A | * 5/1963 | Stalcup | 206/5.1 |
| 3,091,328 A | 5/1963 | Leonardos | |
| 3,268,068 A | * 8/1966 | Grand | 206/5.1 |
| 3,584,908 A | 6/1971 | Ray | |
| 3,647,380 A | 3/1972 | Middleton | |
| 4,232,966 A | 11/1980 | Schpak et al. | |
| 4,545,478 A | 10/1985 | Waldman | |
| 4,750,771 A | 6/1988 | Emmett et al. | |
| 4,753,470 A | 6/1988 | Menard | |
| 4,779,300 A | 10/1988 | Pompe | |
| 5,054,610 A | * 10/1991 | Ajello | 206/5.1 |
| 5,071,276 A | 12/1991 | Nielsen et al. | |
| 5,348,358 A | 9/1994 | Selick | |
| 5,362,294 A | * 11/1994 | Seitzinger | 604/11 |
| 5,382,297 A | * 1/1995 | Valentine et al. | 134/15 |
| 5,395,309 A | * 3/1995 | Tanaka et al. | 604/11 |
| 5,431,879 A | * 7/1995 | Heyl et al. | 206/5.1 |
| 5,439,572 A | * 8/1995 | Pankow | 206/5.1 |
| 5,440,458 A | * 8/1995 | Volk | 206/5.1 |
| 5,447,505 A | * 9/1995 | Valentine et al. | 604/304 |
| 5,456,361 A | * 10/1995 | Walsh et al. | 206/5.1 |
| 5,598,601 A | 2/1997 | Eaton et al. | |
| 5,657,506 A | * 8/1997 | Pankow | 206/5.1 |
| 5,695,049 A | 12/1997 | Bauman | |
| 5,732,990 A | 3/1998 | Yavitz et al. | |
| 5,928,606 A | * 7/1999 | Sugiura | 422/300 |
| 6,134,736 A | * 10/2000 | Pankow | 206/5.1 |
| 6,138,312 A | * 10/2000 | Cummings | 206/5.1 |
| 6,235,125 B1 | * 5/2001 | Cercone et al. | 134/28 |

FOREIGN PATENT DOCUMENTS

DE   3822-654 A   11/1990

* cited by examiner

Primary Examiner—Luan K. Bui
(74) Attorney, Agent, or Firm—Fletcher, Yoder & Van Someren

(57) ABSTRACT

A unique container system for holding and cleaning a soft contact lens over a period of time. The system includes a container base having a substantially dry cavity. A hydrophilic fixation and cleaning member is wetted and disposed within the substantially dry cavity. The contact lens is placed on the hydrophilic fixation member and held in a desired orientation while remaining hydrated due to the moisture from the hydrophilic fixation member. Also, a cover is disposed over the substantially dry cavity to enclose the hydrophilic fixation member and the contact lens during storage.

11 Claims, 3 Drawing Sheets

SOFT CONTACT LENS CLEANING AND STORAGE SYSTEM

FIELD OF THE INVENTION

The present invention relates generally to contact lens containers, and particularly to a unique, soft contact lens holder that utilizes a hydrophilic member to maintain the contact lens in an optimal state during periods of shipment and/or storage.

BACKGROUND OF THE INVENTION

A variety of contact lens cases currently are known and available. Some of the contact lens packages are used for shipping the contact lenses to a desired recipient, such as an end user or optician. Other contact lens holders are designed for use by the contact wearer. These latter holders or cases permit the contact lens to be stored over periods of time, e.g. through the night, when the individual is not wearing the contact lens.

Regardless of the particular contact lens container style, such containers typically include a well or wells for receiving at least one contact lens as well as sufficient saline solution to submerge each contact lens. Generally, the well is enclosed by a cover that is sufficiently sealed to prevent loss of the saline solution.

The advent of soft contact lenses, such as daily wear or disposable contact lenses, has made it imperative, that the lens be maintained in a moist or hydrated condition during periods of non-use. Without the moistening liquid, the thin plastic material of the contact lens rapidly dries and ultimately becomes unusable.

Simply placing a contact lens in a well with an appropriate saline-based solution, however, can be problematic. For example, the use of sufficient saline-based solution to maintain a contact lens submerged requires sufficiently large packaging to accommodate both the contact lens and the well of contact lens solution. This adds to the size and the weight of the contact lens package, which is disadvantageous, particularly for the distribution of large numbers of contact lenses. Furthermore, the use of liquid within the contact lens holder can create messy spills during opening of the package and/or application of the contact lens to an eye of an individual.

Using wells of saline-based solution also creates difficulty in locating and removing the contact lens from its container when a wearer is ready to apply the lens. Furthermore, the size of the well necessary to contain the liquid and contact lens, as well as the free-flowing motion of the liquid, permits inadvertent reorientation of the contact lens while in the container. For example, the contact lens may become inverted in the container, thereby inducing the wearer to apply the contact to his or her eye in an inverted or reverse orientation. This can lead to irritation of the eye and discomfort to the wearer. Additionally, the soft material of the contact lenses can become folded which leads to added difficulty in applying the contact lens to an eye, and also can result in damage to the contact lens.

It would be advantageous to have a contact lens packaging system that would maintain a contact lens in a moist state without incurring the size and use disadvantages of maintaining the contact lens in a well of liquid.

SUMMARY OF THE INVENTION

The present invention features a package for holding a contact lens over a period of time without permitting dehydration of the contact lens. The package includes a container base having a substantially dry cavity. A hydrophilic fixation member is disposed in the substantially dry cavity. Additionally, a contact lens is disposed in the substantially dry cavity. An appropriate liquid is used to wet the hydrophilic fixation member, which absorbs the liquid. A cover encloses the hydrophilic fixation member and the contact lens within the substantially dry cavity.

According to another aspect of the invention, a contact lens container system is provided for maintaining a contact lens in a usable state during a period of storage. The container system includes a sealed container having an internal cavity. A hydrophilic member and a contact lens are disposed in the internal cavity. Additionally, a moistening agent is applied to the hydrophilic member.

According to another aspect of the invention, a method is provided for storing a contact lens. The method includes preparing a container with a cavity of sufficient size to receive a contact lens. The method also includes placing a moisture absorbent member in the cavity, and moistening the absorbent member. Furthermore, the method includes enclosing the contact lens within the cavity.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

Figure 1:
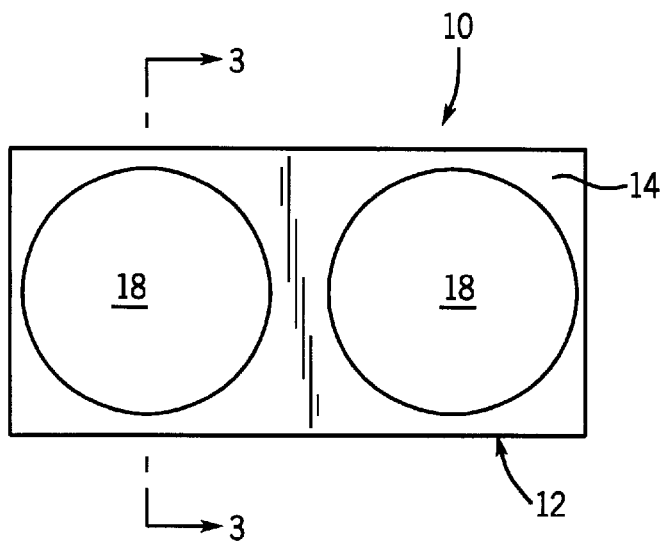
FIG. 1 is a top view of a contact lens container system, according to one preferred embodiment of the present invention.
Figure 2:
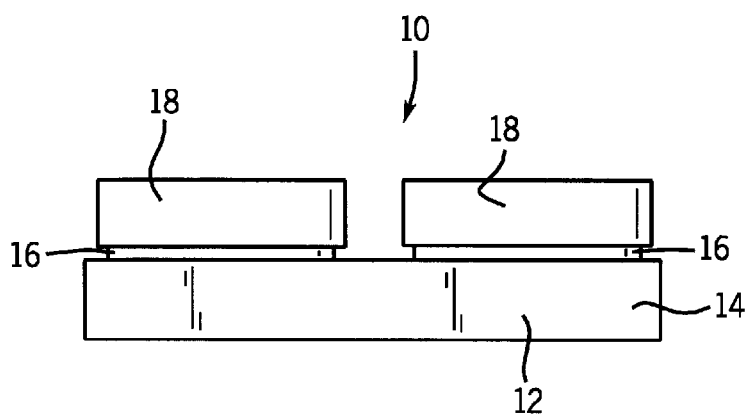
FIG. 2 is a front view of the contact lens container system illustrated in FIG. 1.

Referring generally to FIGS. 1 and 2, a package or container system 10 is illustrated according to one embodiment of the present invention. The exemplary container is used for storing at least one, and typically two contact lenses. Container 10 includes a container base 12 that has an elongate lower portion 14 from which a pair of generally annular walls 16 extend upwardly. A cover 18 is connected to each annular wall 16.

Internally, the elongate lower portion 14, annular walls 16 and covers 18 cooperate to create a pair of internal cavities for receiving and separating, for instance, the left contact lens and the right contact lens of an individual wearer. Both cavities or wells are largely the same, and the description below of an individual well applies equally to the other.

Figure 3:
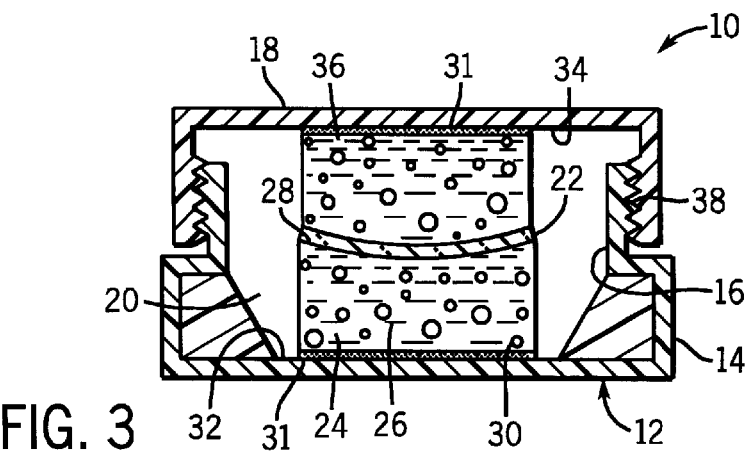
FIG. 3 is a cross-sectional view taken generally along line 3—3 of FIG. 1.

Referring generally to FIG. 3, a cross-sectional view taken generally along line 3—3 of FIG. 1 is provided.

Container base 12 includes at least one and preferably a pair of wells 20, each designed for receiving an individual contact lens 22, typically a soft contact lens. Preferably, well 20 is a substantially dry cavity. Substantially dry cavity refers to the lack of free-flowing liquid that would otherwise reside in the well of a contact lens holding package. The present, unique packaging system does not require the submersion of contact lens 22, even when contact lens 22 comprises a thin plastic, daily-wear or disposable contact lens.

Contact lens 22 is maintained in its moistened or hydrated state by a hydrophilic member 24 disposed in the substantially dry cavity or well 20. Hydrophilic member 24 is designed to hold or retain a liquid 26 when wetted with the liquid. An exemplary liquid 26 is a saline-based solution, such as a buffered saline solution used for the conventional submersion of contact lenses within conventional contact lens containers. Hydrophilic member 24 transmits, by capillary action, sufficient moisture to soft contact lens 22 to maintain the contact lens in a soft and supple condition ready for application to the eye of a wearer. The saline-based solution also may include surfactants and other cleaning agents or sterilizing agents to help maintain lens 22 in a desirable condition.

Preferably, hydrophilic member 24 also serves as a contact lens fixation member that holds contact lens 22 in a desired position. Certain materials have an affinity for the polymeric material of soft contact lens 22 and tend to grip or hold the lens in a desired position within well 20. Additionally, hydrophilic member 24 may have a contoured surface 28 to facilitate the holding of contact lens 22 in a desired orientation.

In the preferred embodiment, hydrophilic member 24 comprises a sponge material 30. It has been determined that a preferred sponge material for holding and maintaining contact lens 22 in a usable state is a Merocel™ sponge material, a polyvinylacetal (PVA) material available from the Solan company, having a place of business at 6743 Southpoint Drive North in Jacksonville, Fla. The Merocel™ sponge material works well, because it is lint free, chemically stable and readily holds liquid 26. The Merocel™ material is able to transfer moisture to contact lens 22 by capillary action while holding contact lens 22 in a desired orientation because of its affinity for the contact lens material. By using Merocel™ sponge material, hydrophilic member 24 is able to maintain contact lens 22 in a ready-to-use state over substantial storage periods of weeks, months or more depending on overall package design.

In the preferred embodiment, hydrophilic member 24 is affixed at a desired location within dry cavity 20 so that contact lens 22 may be held at a desired position or orientation. For example, the hydrophilic member 24 may be affixed by an adhesive 31, such as a glue or a wax, to a lower, interior surface 32 of container base 12. Alternatively, the hydrophilic member 24 can be connected to an interior surface 34 of cover 18.

Furthermore, it also may be desirable to provide a second hydrophilic member 36. In the preferred embodiment, second hydrophilic member 36 also is a sponge material, most preferably the Merocel™ sponge material discussed above. As illustrated, second hydrophilic member 36 is affixed to interior surface 34 of cover 18 such that contact lens 22 is pressed between hydrophilic member 24 and second hydrophilic member 36 when cover 18 is placed over its corresponding annular wall 16.

In the illustrated embodiment, cover 18 is threadably engaged with annular wall 16 via a threaded region 38. Preferably, hydrophilic member 24 and second hydrophilic member 36 engage contact lens 22 during the threading of cover 18 into and out of engagement with container base 12. The Merocel™ sponge material has a substantial cleaning action when rubbed against contact lens 22. Thus, proteins, mucus and other contaminants are removed from contact lens 22 during assembly and disassembly of container 10. Preferably, the threaded engagement of cover 18 with container base 12 also provides a sufficient seal to prevent dissemination of liquid 26 to the exterior of container 10.

Figure 4:
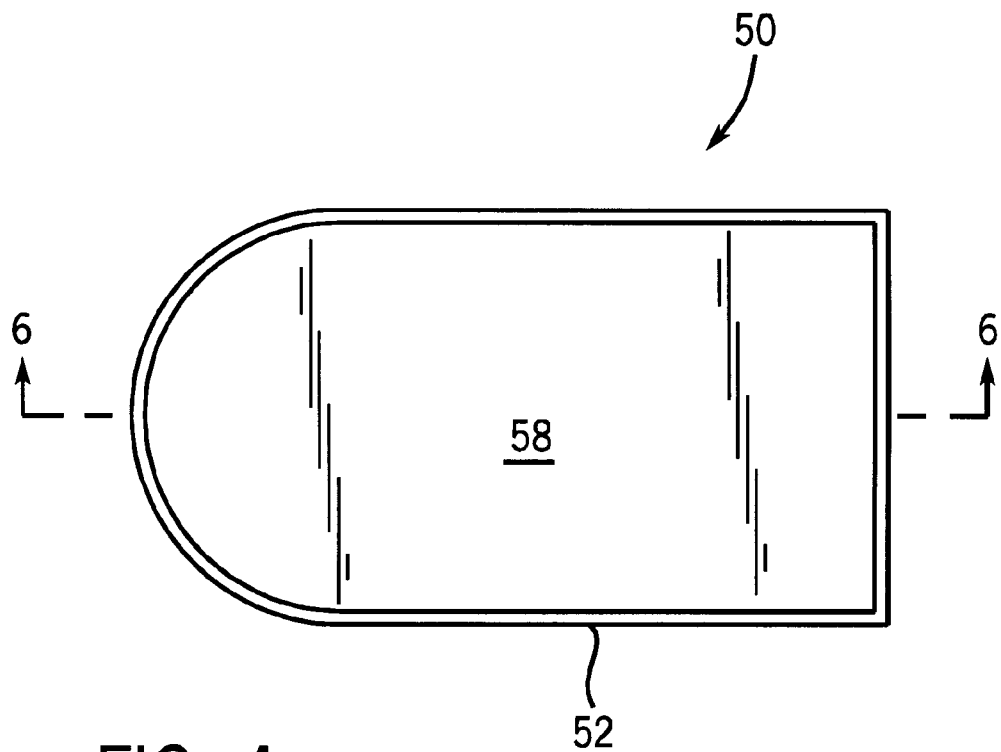
FIG. 4 is a top view of an alternate contact lens container system, according to another preferred embodiment of the present invention.
Figure 5:
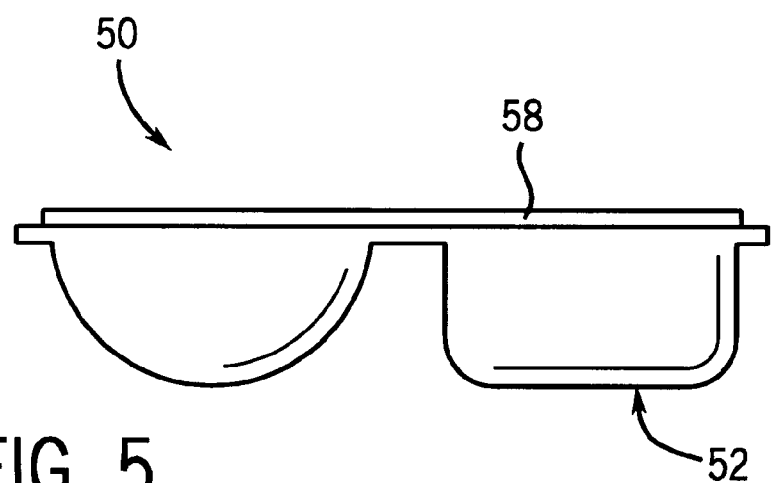
FIG. 5 is a front view of the contact lens container system illustrated in FIG. 4.
Figure 6:
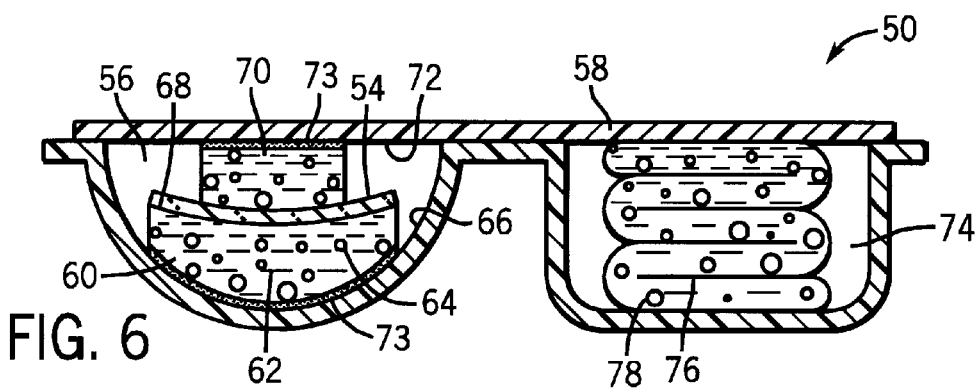
FIG. 6 is a cross-sectional view taken generally along line 6—6 of FIG. 4.

Referring generally to FIGS. 4, 5 and 6, an alternate embodiment of container/package 10 is illustrated and labeled as package 50. In this contact lens container system, a container base 52 is designed to hold at least one contact lens 54, such as a daily-wear or disposable contact lens. Again, container base 52 includes a substantially dry cavity 56 that is enclosed by a cover 58. In this embodiment, the exemplary cover 58 is a peelable style cover that is adhered to container base 52 by heat sealing or an appropriate adhesive to seal and enclose contact lens 54 within cavity 56. This type of package or container 50 might readily be used for shipping contact lenses to a desired recipient.

As illustrated best in FIG. 6, a hydrophilic member 60 is disposed in cavity 56. Hydrophilic member 60 is wetted with a liquid 62, such as a saline solution appropriate for contact lens 54. Preferably, hydrophilic member 60 is a sponge material 64, such as the Merocel™ sponge material.

Although hydrophilic member 60 can be loosely disposed within cavity 56, it is preferred that member 60 be affixed at a specific, desired location within dry cavity 56. By affixing hydrophilic member 60, the positioning and orientation of contact lens 54 may be controlled for ready retrieval and/or application by the contact lens wearer. The optimal location of hydrophilic member 60 will vary with package design and the desired functionality of package 50. By way of example, however, sponge material 64 may be affixed to an interior surface 66 along the lower portion of cavity 56, as illustrated in FIG. 6. As discussed above, hydrophilic member 60 also may include a contoured surface 68, such as a surface designed to match either the convex or concave curvature of contact lens 54.

Furthermore, package 50 may include a second hydrophilic member 70. For example, second hydrophilic member 70 may be attached to an interior surface 72 of cover 58 to engage contact lens 54 on a surface opposite sponge material 64. Second hydrophilic member 70 preferably is formed from the Merocel™ material. Both hydrophilic member 60 and second hydrophilic member 70 may be attached to their respective surfaces by an adhesive 73, such as a glue or a wax.

Optionally, package 50 may include a second cavity 74 designed to contain a cleaning material 76 that may be utilized in scrubbing contact lens 54. Preferably, cleaning material 76 comprises a sheet of material, such as sponge material. In the embodiment illustrated, cover 58 simply is peeled further to expose cavity 74 such that cleaning material 76 may be removed. Additionally, cleaning material 76 may be wetted with a desired liquid, such as a saline-based solution or a solution containing surfactants, to facilitate the cleaning of contact lens 54.

Figure 7:
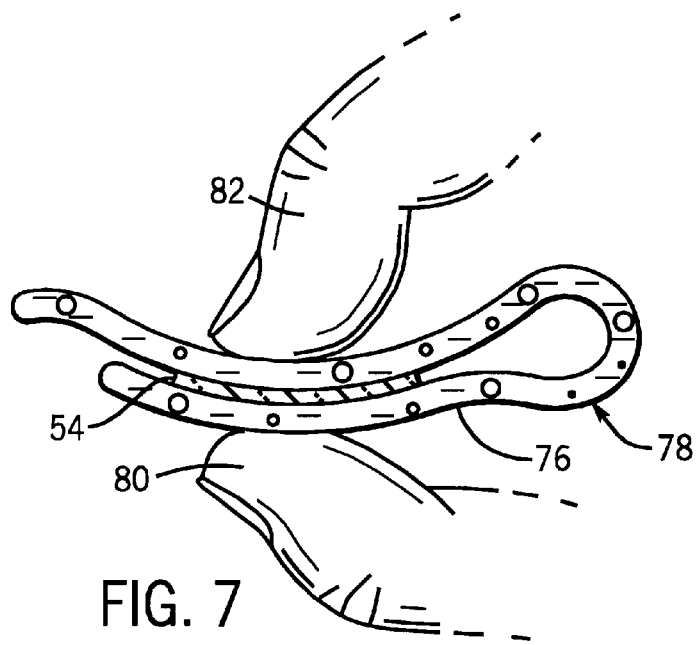
FIG. 7 illustrates the cleaning of a contact lens using a hydrophilic material.

A preferred exemplary cleaning material 76 is a Merocel™ sponge 78. The Merocel™ sponge 78 may be formed in a sheet, such as the sheet illustrated in FIG. 7. Upon removal, the sheet of Merocel™ sponge 78 may be wrapped around contact lens 54 and gripped by a user, e.g. between a thumb 80 and a forefinger 82. It has been determined that the Merocel™ sponge material works extremely well in removing proteins, mucus and other contaminants from contact lens 54 without damaging the contact lens. Sheets of other sponge material having the desired stiffness to remove contaminants without damaging the contact lens may also be available.

Figure 8:
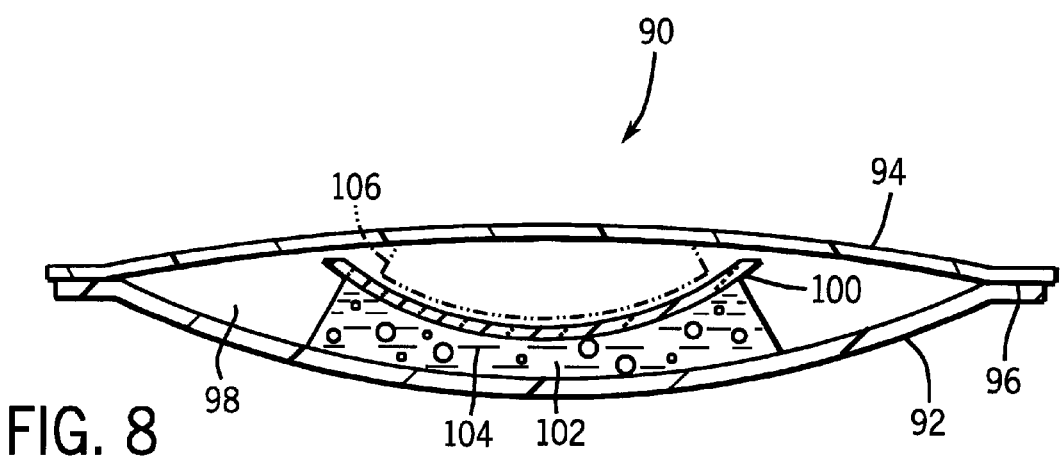
FIG. 8 is a cross-sectional view of another embodiment of the contact lens container system illustrated in FIGS. 1 through 6.

A third exemplary embodiment of package 10 is illustrated in cross-section in FIG. 8. In this embodiment, a container or package 90 is formed from a pair of flexible sheets including a container base sheet 92 and a cover sheet 94. Sheets 92 and 94 are flexible materials that are connected along a perimeter seal 96 to form an internal cavity 98.

Disposed within internal cavity 98 is a contact lens 100 and a hydrophilic member 102. Preferably, hydrophilic member 102 is wetted with an appropriate liquid 104, such as a buffered saline-based solution. Contact lens 100 preferably is disposed adjacent hydrophilic member 102 and is maintained in a moist and usable condition.

Optionally, a second hydrophilic member 106, shown in dashed lines, may be added to contact the contact lens 100 on an opposing surface relative to hydrophilic member 102. Hydrophilic member 102 and second hydrophilic member 106 may have contoured surfaces to match the general contour of contact lens 100. Additionally, hydrophilic member 102 and second hydrophilic member 106 preferably are formed from a sponge material, such as the Merocel™ sponge material described above.

Regardless of the specific configuration of package 10, 50, 90, the use of the hydrophilic member permits construction of a smaller package that contains very little and preferably no free-flowing liquid. This permits the "dry" packaging and storage of contact lenses, and avoids the added container volume, container weight and potential mess necessitated by conventional containers that hold the contact lens in a submerged or at least semi-submerged state within a reservoir of liquid.

It will be understood that the foregoing description is of preferred embodiments of this invention, and that the invention is not limited to the specific forms shown. For example, a variety of materials may be used in construction of the packaging; a variety of hydrophilic member configurations may be utilized, depending on the package and the desired functionality; different liquids may be used to wet the hydrophilic member; and the hydrophilic member may be positioned in a variety of locations to facilitate retrieval and/or application of the contact lens. These and other modifications may be made in the design and arrangement of the elements without departing from the scope of the invention as expressed in the appended claims.

What is claimed is:

1. A contact lens container system for maintain a contact lens in a usable state during a period of storage, comprising:

a sealed container having an internal cavity;

a hydrophilic member disposed in the internal cavity;

a contact lens disposed in the internal cavity on a portion of the surface of the hydrophilic member; and a moistening agent comprising a saline solution applied to the hydrophilic member, further comprising a cleaning material to clean the contact lens, wherein the cleaning material is held by the sealed container.

2. The contact lens container system as recited in claim 1, wherein the hydrophilic member comprises a sponge material.

3. The contact lens container system as recited in claim 2, wherein the sponge material is a polyvinylacetal sponge material.

4. The contact lens container system as recited in claim 1, wherein the hydrophilic member is affixed to the sealed container at a location selected to prevent movement of the contact lens in the internal cavity.

5. The contact lens container system as recited in claim 1, wherein the moistening agent is applied to the hydrophilic member in an amount that is readily retained by the hydrophilic member to prevent the occurrence of free-flowing liquid within the internal cavity.

6. The contact lens container system as recited in claim 1, wherein the cleaning material comprises a sheet of polyvinylacetal sponge material.

7. A method for storing a contact lens, comprising:

preparing a container having a cover and a base container with a cavity of sufficient size to receive a contact lens;

placing a hydrophilic sponge member in the cavity;

moistening the hydrophilic sponge member with a solution comprising saline;

disposing the contact lens within the cavity upon a portion of the surface of the hydrophilic sponge member; and cleaning the contact lens by automatic rubbing of the contact lens and the hydrophilic sponge member during coupling and uncoupling of the cover from the base container.

8. The method as recited in claim 7, wherein placing comprises affixing a sponge to the container.

9. The method as recited in claim 8, further comprising fixating the contact lens at a desired location and in a desired contour.

10. The method as recited in claim 9, further comprising maintaining the cavity in a substantially dry state.

11. The method as recited in claim 10, further comprising forming the sponge from a polyvinylacetal sponge material.

* * * * *